United States Patent
Swoboda et al.

(10) Patent No.: US 12,036,307 B2
(45) Date of Patent: Jul. 16, 2024

(54) BIOSOURCED GELLED COMPOSITION OF HYDROCARBON OIL AND GELLING POLYMER

(71) Applicant: TOTAL MARKETING SERVICES, Puteaux (FR)

(72) Inventors: Benjamin Swoboda, Orgeval (FR); Philippe Conti, Rueil Malmaison (FR); Rachida Francis, Compiègne (FR)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 16/495,749

(22) PCT Filed: Mar. 16, 2018

(86) PCT No.: PCT/EP2018/056773
§ 371 (c)(1),
(2) Date: Sep. 19, 2019

(87) PCT Pub. No.: WO2018/172228
PCT Pub. Date: Sep. 27, 2018

(65) Prior Publication Data
US 2020/0054546 A1    Feb. 20, 2020

(30) Foreign Application Priority Data
Mar. 20, 2017  (EP) .................... 17305307

(51) Int. Cl.
| | | |
|---|---|---|
| *A61K 8/92* | (2006.01) | |
| *A61K 8/04* | (2006.01) | |
| *A61K 8/06* | (2006.01) | |
| *A61K 8/31* | (2006.01) | |
| *A61K 8/36* | (2006.01) | |
| *A61K 8/90* | (2006.01) | |
| *A61K 9/00* | (2006.01) | |
| *A61K 9/06* | (2006.01) | |
| *A61K 9/107* | (2006.01) | |
| *A61K 47/06* | (2006.01) | |
| *A61K 47/12* | (2006.01) | |
| *A61K 47/44* | (2017.01) | |
| *A61Q 19/00* | (2006.01) | |
| *A61Q 19/08* | (2006.01) | |

(52) U.S. Cl.
CPC ............ *A61K 8/92* (2013.01); *A61K 8/042* (2013.01); *A61K 8/062* (2013.01); *A61K 8/064* (2013.01); *A61K 8/31* (2013.01); *A61K 8/361* (2013.01); *A61K 8/90* (2013.01); *A61K 9/0014* (2013.01); *A61K 9/06* (2013.01); *A61K 9/107* (2013.01); *A61K 47/06* (2013.01); *A61K 47/12* (2013.01); *A61K 47/44* (2013.01); *A61Q 19/00* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 2004/0009198 A1* | 1/2004 | Bernard | .................. A61K 8/31 424/401 |
| 2005/0239950 A1* | 10/2005 | Martin | ................. A61K 8/8117 524/502 |
| 2011/0045983 A1 | 2/2011 | Healy et al. | |

FOREIGN PATENT DOCUMENTS

| | | |
|---|---|---|
| DE | 10 2011 088 157 A1 | 6/2013 |
| EP | 0497144 * | 8/1992 |
| EP | 1 584 322 A1 | 10/2005 |
| EP | 1 728 844 A1 | 12/2006 |
| EP | 2 181 694 A1 | 5/2010 |
| EP | 2 368 967 A1 | 9/2011 |
| EP | 3 095 838 A1 | 11/2016 |
| FR | 2 911 497 A1 | 7/2008 |
| JP | 8-73313 A | 3/1996 |
| JP | 2000-26238 A | 1/2000 |
| JP | 2001-503070 A | 3/2001 |
| WO | WO 99/22710 A1 | 5/1999 |
| WO | WO 00/26285 A1 | 5/2000 |
| WO | WO 02/05760 A1 | 1/2002 |
| WO | WO 2008/058664 A1 | 5/2008 |
| WO | WO 2014/033762 A1 | 3/2014 |
| WO | WO 2016/030837 A1 | 3/2016 |
| WO | WO 2016/185046 A1 | 11/2016 |

OTHER PUBLICATIONS

International Search Report, issued in PCT/EP2018/056773, dated Jun. 7, 2018.
Japanese Office Action issued in Application No. 2019-551518, dated Jul. 19, 2022.
English translation of the Japanese Preliminary Report of an Appeal Proceedings for Japanese Application No. 2019-551518 (Appeal No. 2022-018382), dated Feb. 21, 2023.

* cited by examiner

*Primary Examiner* — Tigabu Kassa
(74) *Attorney, Agent, or Firm* — Birch, Stewart, Kolasch & Birch, LLP

(57) ABSTRACT

A gelled composition includes at least 50% by weight of at least one hydrocarbon oil that includes a content by weight of isoparaffins ranging from 90 to 100%, a content by weight of normal paraffins ranging from 0 to 10% and a content of carbon of biological origin greater than or equal to 90% relative to the total weight of the hydrocarbon oil, and at least 1% by weight of at least one gelling agent chosen from among: polymers chosen from homopolymers and copolymers obtained from at least one monomer chosen from among isoprene, butadiene, styrene and (meth)acrylates, and the mixtures of same, and non-polymer gelling agents, relative to the total weight of the gelled composition.

14 Claims, No Drawings

BIOSOURCED GELLED COMPOSITION OF HYDROCARBON OIL AND GELLING POLYMER

FIELD OF THE INVENTION

The invention relates to a gelled composition comprising at least one hydrocarbon oil classed as biodegradable, of biological origin and mostly isoparaffinic.

The invention also relates to a cosmetic, dermatological or pharmaceutical composition comprising said gelled composition and the use thereof.

The present invention also relates to the use of said gelled composition for the formulation of cosmetic products, dermatological products or pharmaceutical products.

TECHNICAL CONTEXT OF THE INVENTION

Cosmetic products exist in different forms. They can be either in the form of emulsions (a mixture between an aqueous phase and a fatty phase stabilised by an emulsifier), or entirely aqueous, or entirely anhydrous (only a fatty phase). In order to add texture or increase the viscosity of the fatty phase, either in an emulsion or in an anhydrous product, those skilled in the art will use a fatty phase gel which is a mixture between an apolar oil and a gelling agent. These gels are particularly used for the formulation of gloss, moisturiser for lips, creme for the skin or sunscreen product. But they are also found in hair care products, depilatory creams and deodorants.

These gels can also have applications in pharmacy, home care and in general industry.

Thus, an apolar gel is a mixture of an apolar oil and of a gelling agent. Apolar oils can be mineral oils, vegetable oils, silicone oils or isoparaffins. The gelling agent is most often polymeric such as the ethylene/propylene styrene copolymer or the butylene/ethylene/styrene copolymer or the polyisobutene, polydecene or isoprene copolymers (or encore SEBS, SBS, SIS, TPE, . . . ). These copolymers are typically sold by the companies Kraton or Kuraray.

The most widespread gels are gels with a mineral oil base. The compatibility between these oils and copolymers is very good, indeed the apolar structure of the copolymers is highly compatible with these oils. The major disadvantages of a gel with a mineral oil base are: the fossil origin of the oil and the stringy texture of the product.

Document WO 02/05760 relates to a cosmetic and/or physiological composition comprising at least one powdery compound and at least one pro-adhesive material. Document EP 1 584 322 relates to an anhydrous cosmetic composition comprising a polymer gelling agent, a non-volatile oil and particles of methyl polymethacrylate. These two documents do not disclose the hydrocarbon oil of biological origin as defined in the present invention.

In order to overcome this disadvantage (fossil or petrochemical origin), gels with a vegetable oil or ester base were studied (for example in the application US2011/0045983 A1). The compatibility between oxygenated oils such as esters or vegetable oils and copolymers is not as good, which can lead to compositions that are difficult to formulate. In addition, the esters are also of chemical origin. As for vegetable oils (effectively of biosourced origin), they have the major disadvantage, in addition to the poor compatibility with copolymers, of becoming rancid, and of being sensitive to oxidation which generally requires the use of an antioxidant. The instability of these vegetable oils comes in particular from the presence, in a substantial quantity, of molecules comprising heteroatoms and/or unsaturations.

There therefore remains the need to have a gelled composition (or gel) that comprises a biosourced fatty phase that has good compatibility between the fatty phase and the gelling compound and which does not require the adding of an antioxidant.

The applicant surprisingly found that this need can be satisfied by a new gelled composition with a fatty phase of biological origin mostly comprising isoparaffins and which makes it possible to propose stable compositions.

The present invention has for objective to provide an isoparaffinic gelled composition coming from raw material of biological origin.

The present invention also has for objective to propose a stable gelled composition with properties that are adapted to the use thereof.

SUMMARY OF THE INVENTION

These objectives are achieved thanks to a new gelled composition. The invention relates to a gelled composition comprising:
- at least 50% by weight of at least one hydrocarbon oil that has a content by weight of isoparaffins ranging from 90 to 100%, a content by weight of normal paraffins ranging from 0 to 10% and a content of carbon of biological origin greater than or equal to 90% relative to the total weight of the hydrocarbon oil, and
- at least 0.5% by weight of at least one gelling agent chosen from among:
  i. gelling polymers chosen from among homopolymers or copolymers comprising at least one monomer chosen from among isoprene, butadiene, styrene and (meth) acrylates,
  ii. non-polymer gelling agents,
  relative to the total weight of the gelled composition.

According to an embodiment of the invention, the gelling agent is a gelling polymer chosen from among homopolymers or copolymers comprising at least one monomer chosen from among isoprene, butadiene, styrene and (meth) acrylates.

According to an embodiment of the invention, the gelling polymer is chosen from among homopolymers or copolymers comprising at least one monomer chosen from among isoprene, butadiene, styrene.

According to an embodiment of the invention, the polymer is a copolymer comprising at least one styrene monomer and at least one monomer chosen from among ethylene, propylene, butadiene, isoprene.

According to an embodiment of the invention, the polymer is chosen from among star polymers, diblock copolymers, triblock copolymers, multiblock copolymers, comb polymers, radial polymers, and combinations of the latter.

According to an embodiment of the invention, the polymer is chosen from among styrene/butadiene copolymers, styrene/isoprene copolymers, hydrogenated styrene/butadiene copolymers, hydrogenated styrene/isoprene copolymers, hydrogenated polyisoprene crosspolymers, polyisoprene homopolymers, hydrogenated styrene thermoplastic homopolymers, liquid rubbers, and mixtures thereof.

According to another embodiment, the gelling agent is a non-polymer gelling agent chosen from among mineral fillers, waxes, ammonium salts and metal salts.

According to an embodiment of the invention, the hydrocarbon oil is chosen from among non-cyclic isoparaffins comprising from 14 to 18 carbon atoms.

According to an embodiment of the invention, the hydrocarbon oil comprises:
- a content by weight of isoparaffins ranging from 90 to 100%, preferably from 95 to 100% and preferentially from 98% to 100% relative to the total weight of the hydrocarbon oil
- a content of carbon of biological origin greater than or equal to 95%, preferably greater than or equal to 98% and preferentially of 100%
- a content by weight of normal paraffins less than or equal to 10, preferably less than or equal to 5% and preferentially less than or equal to 2% relative to the total weight of the hydrocarbon oil; and/or
- a content by weight of naphthenic compounds less than or equal to 1%, preferably less than or equal to 0.5% and preferentially less than or equal to 100 ppm relative to the total weight of the hydrocarbon oil; and/or
- a content by weight of aromatic compounds less than or equal to 500 ppm, preferably less than or equal to 300 ppm, preferentially less than or equal to 100 ppm, more preferentially less than or equal to 50 ppm and advantageously less than or equal to 20 ppm, relative to the total weight of the hydrocarbon oil.

According to an embodiment of the invention, the hydrocarbon oil has:
- a boiling temperature ranging from 230 to 340° C., preferably from 235 to 330° C. and more preferentially from 240 to 325° C. according to the standard ASTM D86; and/or
- a biodegradability at 28 days of at least 60%, preferably of at least 70%, preferentially of at least 75% and even more preferentially of at least 80% measured according to the standard OECD 306; and/or
- a flash point greater than or equal to 110° C. according to the standard EN ISO 2719.

According to an embodiment of the invention, the hydrocarbon oil is obtained by a method of catalytic hydrogenation at a temperature from 80 to 180° C. and at a pressure from 50 to 160 bars of a deoxygenated and/or isomerised feedstock of biological origin.

According to an embodiment of the invention, the gelled composition comprises, relative to the total weight of the gelled composition, from 50 to 99% by weight, preferably from 60 to 95% by weight, more preferably from 70 to 90% by weight, of hydrocarbon oil and from 1 to 50% by weight, preferably from 5 to 40% by weight, more preferably from 10 to 30% by weight, of said gelling agent, preferably chosen from among gelling polymers.

The invention also relates to a cosmetic, dermatological or pharmaceutical composition comprising at least one gelled composition according to the invention, preferably in a quantity ranging from 0.5 to 80%, preferentially from 1 to 50% and advantageously from 5 to 30% by weight relative to the total weight of the composition.

According to an embodiment of the invention, the cosmetic, dermatological or pharmaceutical composition according to the invention comprises:
- at least one fatty substance chosen from among: vegetable oils, hydrocarbon oils other than the hydrocarbon oil of said emollient composition, vegetable butters, fatty alcohols and ethers, oily esters, alkanes and silicone oils and/or
- at least one additive preferably chosen from emulsifiers.

The invention also has for object the use of the gelled composition according to the invention, or of the cosmetic, dermatological or pharmaceutical composition according to the invention for a topical application, in particular as a care product for the skin or hair, as a make-up product, as a hair care product, as a makeup remover, as a perfumed product, as a sunscreen product, as a lip care product, such as a gloss or moisturising sticks for lips.

According to an embodiment of the invention, the gelled composition according to the invention or the cosmetic, dermatological or pharmaceutical composition is used as an anti-ageing agent.

The invention also relates to a method of cosmetic treatment of the skin comprising at least one step of applying, preferably by spreading, the gelled composition according to the invention or of the cosmetic, dermatological or pharmaceutical composition according to the invention.

The invention also has for object a gelled composition according to the invention or a cosmetic, dermatological or pharmaceutical composition according to the invention, for use as a drug.

According to an embodiment, the gelled composition according to the invention or the cosmetic, dermatological or pharmaceutical composition according to the invention is used as an antioxidant and/or anti-radical agent and/or anti-inflammatory agent and/or anti-apoptotic and/or antibacterial and/or antifungal agent.

DETAILED DESCRIPTION OF THE INVENTION

The invention relates to a gelled composition comprising:
- at least 50% by weight of at least one hydrocarbon oil that has a content by weight of isoparaffins ranging from 90 to 100%, a content by weight of normal paraffins ranging from 0 to 10% and a content of carbon of biological origin greater than or equal to 90% relative to the total weight of the hydrocarbon oil, and
- at least 0.5% by weight of at least one gelling agent chosen from among:
  i. polymers chosen from among homopolymers and copolymers obtained from at least one monomer chosen from among styrene, isoprene, butadiene and (meth)acrylates, and
  ii. non-polymer gelling agents chosen preferably from among mineral fillers, waxes, ammonium salts and metal salts, relative to the total weight of the gelled composition.

The gelled composition according to the invention makes it possible to have a composition classed as non-irritating, biodegradable and non-odorous.

The gelled composition according to the invention makes it possible in particular to obtain stable cosmetic, dermatological or pharmaceutical compositions. The stability comes in particular from the fact that the hydrocarbon oil defined in the present invention comprises low proportions, even is substantially or entirely free, of unsaturated compounds and/or of compounds that comprise heteroatoms.

On a preliminary basis it shall be noted that, in the description and the following claims, the expression "between" must be understood as including the limits mentioned.

Gelled Composition:

According to an embodiment of the invention, the gelled composition according to the present invention comprises:
- from 50 to 99.5% by weight, more preferably from 60 to 99% by weight, preferentially from 70 to 98% by weight, more preferentially from 80 to 95% by weight, even more preferentially from 85 to 93% by weight, of hydrocarbon oil, and from 0.5 to 50% by weight, preferably from 1 to 40% by weight, preferentially from 2 to 30% by weight, more preferentially from 5 to 20% by weight, even more preferentially from 7 to 15% by weight, of gelling agent(s).

According to an embodiment of the invention, the gelled composition according to the present invention comprises:
from 50 to 99.5% by weight, more preferably from 60 to 99% by weight, preferentially from 70 to 98% by weight, more preferentially from 80 to 95% by weight, even more preferentially from 85 to 93% by weight, of hydrocarbon oil, and
from 0.5 to 50% by weight, preferably from 1 to 40% by weight, preferentially from 2 to 30% by weight, more preferentially from 5 to 20% by weight, even more preferentially from 7 to 15% by weight, of gelling polymer(s) chosen from among homopolymers and copolymers comprising at least one monomer chosen from among isoprene, butadiene, styrene and (meth) acrylates.

According to an embodiment of the invention, the gelled composition has a viscosity measured at 23° C. (according to a method described in the experimental part) ranging from 3 to 750,000 mPa·s.

Thus, the gelled composition according to the invention will more preferably comprise a single fatty phase.

Hydrocarbon Oil:

The gelled composition according to the invention more preferably comprises a content of hydrocarbon oil ranging from 50 to 99.5% by weight, preferentially from 60 to 99% by weight, more preferentially from 70 to 98% by weight and advantageously from 80 to 95% by weight relative to the total weight of the composition.

The presence of a significant quantity of hydrocarbon oil according to the invention contributes to the cosmetic, pharmaceutical and/or dermatological qualities of the gelled composition: pleasant feel, care, shine and protection of the skin.

The hydrocarbon oil of the gelled composition according to the invention preferably comprises a content by weight of isoparaffinic compounds greater than or equal to 90%, preferentially greater than or equal to 95% and advantageously greater than or equal to 98% relative to the total weight of the hydrocarbon oil.

According to an embodiment, the isoparaffinic compounds present in the hydrocarbon oil used according to the invention comprise from 12 to 30 carbon atoms, preferably from 13 to 19 carbon atoms, more preferably from 14 to 18 carbon atoms.

The hydrocarbon oil of the gelled composition according to the invention preferably comprises a content by weight of normal paraffins less than or equal to 10%, preferentially less than or equal to 5% and advantageously less than or equal to 2%.

The hydrocarbon oil of the gelled composition according to the invention advantageously comprises a majority of isoparaffins and a minority of normal paraffins. These isoparaffins are advantageously non-cyclic isoparaffins. More preferably the hydrocarbon oil of the gelled composition has an isoparaffin to normal paraffin mass ratio of at least 12:1, preferentially of 15:1, and more preferentially of 20:1. Even more advantageously the hydrocarbon oil of the gelled composition according to the invention does not contain any normal paraffins.

According to an embodiment, the hydrocarbon oil according to the invention preferably comprises a content by weight of isoparaffins ranging from 90 to 100% and a content in normal paraffins ranging from 0 to 10%, preferentially from 95 to 100% of isoparaffins and from 0 to 5% of normal paraffins and more preferentially from 98% to 100% of isoparaffins and from 0 to 2% of normal paraffins.

According to an embodiment, the hydrocarbon oil of the gelled composition according to the invention preferably comprises a content by weight of isoparaffins ranging from 90 to 100% and a content in normal paraffins ranging from 0 to 10%, preferentially from 95 to 100% of isoparaffins chosen from among the alkanes comprising from 12 to 30 carbon atoms, more preferably from 14 to 18 carbon atoms, more preferably from 14 to 17 carbon atoms.

According to an embodiment, the hydrocarbon oil implemented according to the invention comprises:
isoparaffins having 15 carbon atoms and isoparaffins having 16 carbon atoms in a combined quantity ranging from 80 to 98% by weight, relative to the total weight of the hydrocarbon oil, or
isoparaffins having 16 carbon atoms, isoparaffins having 17 carbon atoms and isoparaffins having 18 carbon atoms in a combined quantity ranging from 80 to 98% by weight, relative to the total weight of the hydrocarbon oil, or
isoparaffins having 17 carbon atoms and isoparaffins having 18 carbon atoms in a combined quantity ranging from 80 to 98% by weight, relative to the total weight of the hydrocarbon oil.

The hydrocarbon oil of the gelled composition according to the invention preferably comprises a content by weight of naphthenic compounds less than or equal to 1%, preferentially less than or equal to 0.5% and more preferentially less than or equal to 100 ppm.

According to another preferred embodiment, the hydrocarbon oil of the gelled composition according to the invention comprises a content by weight of isoparaffins ranging from 90 to 100%, a content by weight of normal paraffins ranging from 0 to 10% and a content by weight of naphthens less than or equal to 1%. Preferentially the hydrocarbon oil comprises a content by weight ranging from 95 to 100% of isoparaffins, from 0 to 5% of normal paraffins and a content by weight of naphthens less than or equal to 0.5%. More preferentially it comprises a content by weight ranging from 98% to 100% of isoparaffins, from 0 to 2% of normal paraffins and a content by weight of naphthens less than or equal to 100 ppm.

The hydrocarbon oil implemented in the gelled composition according to the invention is advantageously free from aromatic compounds. For example, a content by weight of aromatic compounds is understood less than or equal to 500 ppm, preferably less than or equal to 300 ppm, preferentially less than or equal to 100 ppm, more preferentially less than or equal to 50 ppm and advantageously less than or equal to 20 ppm measured for example by UV spectrometry.

The content by weight of isoparaffins, n-paraffins, naphthens and/or aromatics of the hydrocarbon oil can be determined according to methods well known to those skilled in the art. Mention can be made by way of a non-limiting example, a method by gas chromatography.

According to another preferred embodiment, the hydrocarbon oil of the gelled composition according to the invention comprises a content by weight of isoparaffins ranging from 90 to 100%, a content by weight of normal paraffins ranging from 0 to 10%, a content by weight of naphthens less than or equal to 1% and a content by weight of aromatic compounds less than or equal to 500 ppm. Preferentially the hydrocarbon oil comprises a content by weight ranging from 95 to 100% of isoparaffins, from 0 to 5% of normal paraffins, a content by weight of naphthens less than or equal to 0.5% and a content by weight of aromatic compounds less than or equal to 300 ppm, preferably less than 100 ppm, preferentially less than 50 ppm and advantageously less than 20 ppm. Also preferentially the hydrocarbon oil comprises a content by weight ranging from 95 to 100% of isoparaffins, from 0 to 5% of normal paraffins and a content by weight of aromatic compounds less than or equal to 100 ppm. More preferentially it comprises a content by weight ranging from 98% to 100% of isoparaffins, from 0 to 2% of normal paraffins, a content by weight of naphthens less than or equal to 100 ppm and a content by weight of aromatic compounds less than or equal to 100 ppm.

The hydrocarbon oil implemented in the gelled composition according to the invention also preferably has an extremely low content by weight of sulphur compounds, typically less than or equal to 5 ppm, preferentially less than or equal to 3 ppm and more preferentially less than or equal to 0.5 ppm at a level that is too low to be detected using conventional low-content sulphur analysers.

The hydrocarbon oil implemented in the gelled composition according to the invention also has more preferably a flash point greater than or equal to 110° C., preferentially greater than or equal to 120° C. and more preferentially greater than or equal to 140° C. according to the standard EN ISO 2719. A high flash point, typically greater than 110° C. making it possible among other things to overcome on the one hand the problems of safety during the storage and transport by avoiding a flammability that is too sensitive of the hydrocarbon oil.

The hydrocarbon oil also has more preferably a vapour pressure at 20° C. less than or equal to 0.01 kPa.

According to an embodiment, the hydrocarbon oil implemented in the gelled composition according to the invention also has more preferably a flash point greater than or equal to 110° C. according to the standard EN ISO 2719 and a vapour pressure at 20° C. less than or equal to 0.01 kPa. Preferentially the hydrocarbon oil has a flash point greater than or equal to 120° C. and a vapour pressure at 20° C. less than or equal to 0.01 kPa. And more preferentially, it has a flash point greater than or equal to 130° C. and a vapour pressure at 20° C. less than or equal to 0.01 kPa.

The hydrocarbon oil implemented in the gelled composition according to the invention has boiling temperatures, a flash point and a vapour pressure that make it possible to overcome the problems of flammability, odour and volatility.

The hydrocarbon oil of the gelled composition according to the invention furthermore has a kinematic viscosity at 40° C. less than or equal to 5 cSt, preferentially less than or equal to 4 cSt and more preferentially less than or equal to 3 cSt according to the standard EN ISO 3104.

Method for Obtaining Hydrocarbon Oil:

Such compositions of hydrocarbon oils can be obtained in the following way. The hydrocarbon oil according to the invention is a hydrocarbon fraction which comes from the conversion of biomass.

The term "coming from the conversion of biomass" means a hydrocarbon fraction produced from raw materials of biological origin.

Preferably, the hydrocarbon fraction of biological origin is obtained by a method comprising steps of hydrodeoxygenation (HDO) and of isomerisation (ISO). The step of hydrodeoxygenation (HDO) leads to the decomposition of the structures of the biological esters or of the triglyceride constituents, to the elimination of the oxygenated, phosphorus and sulphur compounds and to the hydrogenation of the olefinic bonds. The product coming from the hydrodeoxygenation reaction is then isomerised. A step of fractionation can preferably follow the steps of hydrodeoxygenation and of isomerisation. Advantageously, the fractions of interest are then subjected to steps of hydrotreatment then of distillation in order to obtain the specifications of the hydrocarbon oil desired according to the invention.

This HDO/ISO method is implemented on a raw biological feedstock, also called biomass or raw material of biological origin, selected from the group consisting of vegetable oils, animal fats, fish oils and mixtures thereof. The suitable raw materials of biological origin are for example rapeseed oil, canola oil, tallol, sunflower oil, soybean oil, hempseed oil, olive oil, linseed oil, mustard oil, palm oil, groundnut oil, castor oil, coconut oil, animal fats such as tallow, recycled dietary fats, genetically engineered raw materials, and biological raw materials produced from microorganisms such as algae and bacteria. Condensation products, esters or other derivatives obtained from raw biological materials can also be used as raw materials.

Preferably, the raw material of biological origin is an ester or a triglyceride derivative. This material is subjected firstly to a step of hydrodeoxygenation (HDO) in order to decompose the structure of the component esters or triglycerides and eliminate the oxygenated, phosphorous and sulphur compounds concurrently to the hydrogenation of the olefinic bonds. This step of hydrodeoxygenation (HDO) of the raw material of biological origin is followed by an isomerisation of the product thus obtained leading to the branching of the hydrocarbon chain and by an improvement in the properties of the paraffin at low temperatures.

During the HDO step, the hydrogen and the raw material of biological origin are passed over a catalytic hydrodeoxygenation bed simultaneously or counter-current. During the HDO step, the pressure and the temperature are between 20 and 150 bars and between 200 and 500° C. respectively. Conventional and known hydrodeoxygenation catalysts are used during this step. Optionally, the raw material of biological origin can be subjected to a pre-hydrogenation under mild conditions in order to prevent the secondary reactions of double bonds before the HDO step. After the step of hydrodeoxygenation, the product coming from the reaction is subjected to a step of isomerisation (ISO) where the hydrogen and the product, and optionally a mixture of n-paraffins, are passed over catalytic hydrodeoxygenation beds simultaneously or counter-current. During the ISO step, the pressure and the temperature are between 20 and 150 bars and between 200 and 500° C. respectively. Conventional and known isomerisation catalysts are used during this step.

Additional secondary methods can also be implemented (such as intermediate mixtures, trappings or other methods of the sort).

The product coming from the HDO/ISO steps can optionally be fractionated in order to obtain the fractions of interest.

Various HDO/ISO methods are described in literature. Application WO2014/033762 describes a method that comprises a step of pre-hydrogenation, a step of hydrodeoxygenation (HDO) and a step of isomerisation carried out counter-current. Patent application EP1728844 describes a method of producing hydrocarbon compounds from a mixture of compounds of plant and animal origin. This method comprises a step of pretreating the mixture that makes it possible to remove the contaminants, such as for example alkali metal salts, followed by a step of hydrodeoxygenation (HDO) and by a step of isomerisation. Patent application EP2084245 describes a method for producing a hydrocarbon mixture that can be used as diesel or in a composition of diesel by hydrodeoxygenation of a mixture of biological origin that contains fatty acid esters optionally in a mixture with free fatty acids, for example vegetable oils such as sunflower oil, rapeseed oil, canola oil, palm oil or pine oil, followed by a hydroisomerisation on specific catalysts. Patent application EP2368967 describes such a method and the product obtained by this method. Application WO2016/185046 describes a method for obtaining a hydrocarbon oil used according to the invention, wherein the hydrocarbon oil is obtained by a method of catalytic hydrogenation at a temperature from 80 to 180° C. and at a pressure from 50 to 160 bars of a deoxygenated and isomerised feedstock of biological origin.

Advantageously, the raw material of biological origin contains less than 15 ppm of sulphur, preferably less than 8 ppm, preferentially less than 5 ppm and more preferentially less than 1 ppm according to the standard EN ISO 20846. Ideally, the feedstock does not contain any sulphur as a raw material of biosourced origin.

Before the step of hydrotreatment, a step of pre-fractionating can take place. A narrower fraction at the input of the hydrogenation unit makes it possible to obtain a narrow fraction at the output of the unit. Indeed, the boiling points of pre-fractionated fractions are between 220 and 330° C. while the fractions that were not pre-fractionated typically have boiling points between 150 and 360° C.

The deoxygenated and isomerised feedstock coming from the HDO/ISO method is then hydrogenated.

The hydrogen used in the hydrogenation unit is typically highly purified hydrogen. The term "highly purified" means hydrogen of a purity for example greater than 99%, although other grades can also be used.

The step of hydrogenation is carried out thanks to catalysts. The typical hydrogenation catalysts can be either by mass or supported and can include the following metals: nickel, platinum, palladium, rhenium, rhodium, nickel tungstate, nickel-molybdenum, molybdenum, cobalt-molybdenum. The supports can be silica, alumina, silica-alumina or zeolites.

A preferred catalyst is a catalyst with a nickel base on an alumina support of which the specific surface area varies between 100 and 200 $m^2/g$ of catalysts or a mass catalyst based on nickel. The hydrogenation conditions are typically as follows:
  Pressure: 50 to 160 bars, preferably 80 to 150 bars and more preferentially 90 to 120 bars;
  Temperature: 80 to 180° C., preferably 120 to 160° C. and more preferentially 150 to 160° C.;
  Liquid Hourly Space velocity (LHSV): 0.2 to 5 $hr^{-1}$, preferably 0.4 to 3 $hr^{-1}$ and more preferentially 0.5 to 0.8 $hr^{-1}$;
  Treatment rate with hydrogen: adapted to the conditions mentioned hereinabove and able to range up to 200 $Nm^3$/tonne of feedstock to be treated.

The temperature in the reactors is typically between 150 and 160° C. with a pressure of about 100 bars while the hourly space velocity is about 0.6 $hr^{-1}$ with a treatment rate adapted according to the quality of the feedstock to be treated and the parameters of the first hydrogenation reactor.

The hydrogenation can take place in one or several reactors in series. The reactors can include one or several catalytic beds. The catalytic beds are generally stationary catalytic beds.

The method of hydrogenation preferably comprises two or three reactors, preferably three reactors and is more preferentially carried out in three reactors in series.

The first reactor allows for the trapping of the sulphur compounds and the hydrogenation of substantially all the unsaturated compounds and up to about 90% of the aromatic compounds. The product coming from the first reactor contains substantially no sulphur compound. At the second stage i.e. in the second reactor, the hydrogenation of the aromatics continues and up to 99% of the aromatics are therefore hydrogenated.

The third stage in the third reactor is a finishing stage that makes it possible to obtain contents in aromatics less than or equal to 500 ppm, preferably less than or equal to 300 ppm, preferentially less than or equal to 100 ppm, more preferentially less than or equal to 50 ppm, and ideally less than or equal to 20 ppm even in the case of products with a high boiling point for example greater than 300° C.

It is possible to use a reactor that has two or three or more catalytic beds. The catalysts can be present in variable or essentially equal quantities in each reactor; for three reactors, the quantities according to the weight can for example be of 0.05-0.5/0.10-0.70/0.25-0.85, preferably 0.07-0.25/0.15-0.35/0.4-0.78 and more preferentially from 0.10-0.20/0.20-0.32/0.48-0.70.

It is also possible to use one or two hydrogenation reactors instead of three.

It is also possible that the first reactor be comprised of twin reactors implemented alternatively. This method of operability allows in particular a facilitated loading and unloading of the catalysts: when the first reactor comprises the catalyst saturated first (substantially all the sulphur is trapped on and/or in the catalyst) it has to be changed often.

A single reactor can also be used in which two, three or more catalytic beds are installed.

It may be necessary to insert quench boxes into the recycling system or between the reactors in order to cool the effluents from one reactor to another or from one catalytic bed to another in order to control the temperatures and the hydrothermal balance of each reaction. According to a preferred embodiment, there are no cooling or quenching intermediaries.

According to an embodiment, the product coming from the method and/or the separated gases are at least partially recycled in the feeding system of the hydrogenation reactors. This dilution contributes in maintaining the exothermicity of the reaction in controlled limits, in particular in the first stage. The recycling furthermore allows for a heat exchange before the reaction and also a better control of the temperature.

The effluent of the hydrogenation unit mainly contains the hydrogenated product and hydrogen. Flash separators are used to separate the effluents into the gaseous phase, mainly residual hydrogen, and into the liquid phase, mainly the hydrogenated hydrocarbon fractions. The method can be carried out by using three flash separators, at a high pressure, one at an intermediate pressure and one at a low pressure very close to the atmospheric pressure.

The gaseous hydrogen which is collected at the top of the flash separators can be recycled in the feeding system of the hydrogenation unit or at different levels in the hydrogenation units between the reactors.

According to an embodiment, the final product is separated at atmospheric pressure. It then directly feeds a vacuum fractionation unit. Preferably, the fractionating will take place at a pressure between 10 and 50 mbars and more preferentially at about 30 mbars.

The fractionating can be carried out in such a way that it is possible to simultaneously remove various hydrocarbon fluids from the fractionating column and in that their boiling temperature can be predetermined.

By adapting the feedstock through its initial and final boiling points, the hydrogenation reactors, the separators and the fractionation unit can therefore be connected directly without it being necessary to use intermediate tanks. This integration of the hydrogenation and of the fractionating allows for an optimised thermal integration combined with a reduction in the number of devices and energy savings.

The hydrocarbon oil implemented in the gelled composition of the invention is advantageously a hydrocarbon fraction that has a distillation range DR (in ° C.) ranging from 230° C. to 340° C., preferably from 235° C. to 330° C. and more preferentially from 240° C. to 325° C. measured according to the standard ASTM D86. Preferably, the difference between the initial boiling point and the final boiling point is less than or equal to 80° C., preferentially less than or equal to 70° C., more preferentially less than or equal to 60° C. and advantageously between 40 and 50° C. The hydrocarbon oil can include one or several fractions of distillation ranges within the ranges described hereinabove.

Advantageously, the hydrocarbon oil implemented in the gelled composition of the invention is totally saturated. Preferably, the components of the hydrocarbon oil are chosen from among the isoparaffins that comprise 12 to 30 carbon atoms, preferentially 13 to 19 carbon atoms and more preferentially 14 to 18 carbon atoms.

The gelled composition according to the invention advantageously comprises a content by weight of isohexadecane less than or equal to 50%.

The hydrocarbon oil of the gelled composition according to the invention ideally comes from the treatment of raw materials of biological origin. The term "bio-carbon" indicates that the carbon is of natural origin and comes from a biomaterial, as indicated hereinafter. The content in bio-carbon and the content in biomaterial are expressions that indicate the same value. A material of renewable origin or biomaterial is an organic material wherein the carbon comes from the $CO_2$ fixed recently (on a human scale) by photosynthesis from the atmosphere. A biomaterial (Carbon of 100% natural origin) has an isotopic ratio $^{14}C/^{12}C$ greater than $10^{-12}$, typically about $1.2\times10^{-12}$, while a fossil material has a zero ratio. Indeed, the isotopic $^{14}C$ is formed in the atmosphere and is then integrated via photosynthesis, according to a time scale of a few tens of years at most. The half-life of the $^{14}C$ is 5,730 years. Thus, the materials coming from photosynthesis, namely plants in general, necessarily have a maximum content in isotope $^{14}C$.

The determination of the content of biomaterial or of bio-carbon is given in accordance with the standards ASTM D 6866-12, the method B (ASTM D 6866-06) and ASTM D 7026 (ASTM D 7026-04). The hydrocarbon oil of the gelled composition according to the invention has a content of in biomaterial of at least 90%. This content is advantageously higher, in particular greater than or equal to 95%, preferably greater than or equal to 98% and advantageously equal to 100%.

In addition to a particularly high content of biomaterial, the hydrocarbon oil of the gelled composition according to the invention has a particularly good biodegradability. The biodegradation of an organic chemical product refers to the reduction in the complexity of the chemical compounds thanks to the metabolic activity of microorganisms. In aerobic conditions, the microorganisms transform the organic substances into carbon dioxide, water and biomass. The method OECD 306, is used for the evaluation of the biodegradability of individual substances in sea water.

According to this method, the hydrocarbon oil has a biodegradability at 28 days of at least 60%, preferably of at least 70%, more preferably of at least 75%, and advantageously of at least 80%.

Gelling Agent(s) of the Polymer and Non-Polymer Type:

The gelled composition according to the invention can include one or several gelling agents, of the gelling polymer or non-polymer gelling agent type, thus making it possible to gel the hydrocarbon oil.

The term "gelling polymer", according to the present invention, must be understood as to include a polymer that is able to form a gelled composition or gel from an apolar oil that includes the hydrocarbon oils defined in the invention.

The term "non-polymer gelling agent", according to the present invention, must be understood as to include a compound that is different from a polymer and which is able to form a gelled composition or gel from an apolar oil that includes the hydrocarbon oils defined in the invention.

The gelling agent or agents can represent from 0.5 to 50% by weight, preferably from 1 to 40% by weight, more preferably from 5 to 30% by weight, of the total weight of the gelled composition.

The gelling polymer implemented in the gelled composition according to an embodiment of the invention is chosen from among the homopolymers and copolymers comprising at least one monomer chosen from among isoprene, butadiene, styrene and (meth)acrylates, and mixtures thereof.

The term "homopolymer", according to the present invention, must be understood as to include a polymer obtained from a single and same monomer.

The term "copolymer", according to the present invention, must be understood as to include a polymer obtained from at least two different monomers.

The term "homopolymers comprising at least one monomer chosen from among isoprene, butadiene, styrene and (meth)acrylates", according to the present invention, must be understood as to include polyisoprenes, polybutadienes, polystyrenes and (meth)acrylate homopolymers.

The term "copolymers comprising at least one monomer chosen from among isoprene, butadiene, styrene and (meth) acrylates", according to the present invention, must be understood as to include the copolymers obtained from at least one monomer chosen from among isoprene, butadiene, styrene and (meth)acrylates. The copolymers implemented in the gelled composition according to the invention can include other types of monomers.

The polymer implemented in the gelled composition according to an embodiment of the invention can for example have the form of a solution, of an aqueous suspension or of a dispersion.

According to an embodiment, the polymer is chosen from among star polymers, diblock copolymers, triblock copolymers, multiblock copolymers, comb polymers, radial polymers, and combinations of the latter.

According to an embodiment of the invention, the gelling polymer is chosen from among homopolymers or copolymers comprising at least one monomer chosen from among isoprene, butadiene, styrene.

According to an embodiment, the gelling polymer comprises at least one styrene monomer. According to an embodiment, the content by weight of styrene unit of the polymer implemented according to the invention ranges from 5 to 50%, more preferably from 10 to 40%, relative to the total weight of the polymer.

According to an embodiment, the gelling polymer is chosen from among styrene monomers and from one or several monomers chosen from among ethylene, propylene, butadiene, isoprene.

According to an embodiment of the invention, the polymer is chosen from among styrenic block copolymers, comprising more preferably at least one elastomer block. Preferably, the styrenic block copolymer is selected from the group consisting of SIS (polystyrene-polyisoprene-polystyrene), SIBS (polystyrene-polyisoprene-polybutadiene-polystyrene), SBS (polystyrene-polybutadiene-polystyrene), SEBS (polystyrene-poly(ethylenebutylene)-polystyrene) and SEPS (polystyrene-poly(ethylenepropylene)-polystyrene). Such polymers are for example available from the company Kraton, through the commercial products Kraton® G1702 (SEP), G1650 (SEBS), D1101 (mixture of SEBS and SEP).

According to an embodiment of the invention, the polymer is chosen from among homopolymers and copolymers obtained from isoprene. The polymer can for example be chosen from among polyisoprenes. Such polymers are for example available from the company Kraton, through the commercial products Kraton® G 1750 (EP) or Cariflex® IR.

According to a particular embodiment of the invention, the polymer is chosen from among styrene/butadiene copolymers, styrene/isoprene copolymers, hydrogenated styrene/butadiene copolymers, hydrogenated styrene/isoprene copolymers, hydrogenated polyisoprene crosspolymers, polyisoprene homopolymers, hydrogenated styrene thermoplastic homopolymers, liquid rubbers, and mixtures thereof.

The polymer can represent from 0.5 to 50% by weight, preferably from 1 to 40% by weight, more preferably from 5 to 30% by weight, of the total weight of the gelled composition.

According to another embodiment of the invention, the gelling agent is a non-polymer gelling agent chosen preferably from among mineral fillers, waxes, ammonium salts and metal salts, more preferably from among mineral fillers, waxes and metal salts.

Among the mineral fillers that can be used, mention can be made of clays, montmorillonites, silicates such as aluminium silicates, silicas and hectorites. The surface of the mineral fillers may or may not be modified, and in the case of a surface modification, the surface modification can be carried out using grafts of biological or non-biological origin.

Among the waxes (non-polymer) that can be used, mention can be made of natural waxes such as vegetable waxes, animal waxes, ozokerites and ceresin waxes. The vegetable waxes can be chosen from among shea, camellia, sunflower, candelilla, carnauba waxes. The animal waxes can be chosen from among beeswax.

Among the metal salts, mention can be made of zinc stearate.

According to an embodiment of the invention, the gelling agent is a non-polymer gelling agent chosen from among:
 mineral fillers chosen from among clays, montmorillonites, aluminium silicates, silicas and hectorites,
 waxes chosen from among vegetable waxes, animal waxes, ozokerites and ceresin waxes,
 metal salts.

The non-polymer gelling agent can represent from 0.5 to 50% by weight, preferably from 1 to 40% by weight, more preferably from 5 to 30% by weight, of the total weight of the gelled composition.

According to an embodiment of the invention, the gelled composition comprising at least one polymer gelling agent as defined in the present invention and at least one non-polymer gelling agent.

The gelled composition according to the invention is more preferably non-aqueous.

According to an embodiment, the gelled composition is more preferably substantially free from antioxidant, in other words, the gelled composition comprises preferably less than 150 ppm by weight of antioxidant, even more preferably less than 100 ppm by weight of antioxidant, even more preferably is entirely free of antioxidant, with the antioxidant able to be chosen from among compounds of the hindered phenol type, such as BHT (2,6-di-tert-butyl-4-methylphenol).

According to an embodiment of the invention, the gelled composition consists of one or several hydrocarbon oils as defined hereinabove and in one or several gelling agents as defined hereinabove.

According to an embodiment of the invention, the gelled composition consists of at least one hydrocarbon oil as defined hereinabove and of at least one polymer as defined hereinabove.

The invention relates to a gelled composition as defined hereinabove, more preferably except for a composition consisting of:
 a mixture comprising for 100% of its mass:
  i) 3.7% of linear alkanes comprising from 15 to 19 carbon atoms,
  ii) 96% of iso-alkanes comprising from 15 to 19 carbon atoms,
  iii) 0.3% of cyclo-alkanes comprising from 15 to 19 carbon atoms,
 and a hydroxyethyl acrylate copolymer/acryloyldimethyltaurate acrylate copolymer (INCI name),
 with the mixture/copolymer mass ratio being 15/2;
 and/or except for a composition consisting of:
 a mixture $M'_1$ comprising for 100% of its mass:
  i) 3.7% of linear alkanes comprising from 15 to 19 carbon atoms,
  ii) 96%% of iso-alkanes comprising from 15 to 19 carbon atoms,
  iii) 0.3% of cyclo-alkanes comprising from 15 to 19 carbon atoms,
 a mixture $M'_2$ comprising for 100% of its mass:
  i) 13.20% by weight of linear alkanes comprising from 15 to 19 carbon atoms,
  ii) 55.00% by weight of iso-alkanes comprising from 15 to 19 carbon atoms,
  iii) 31.80% of cyclo-alkanes comprising from 15 to 19 carbon atoms,
 and a hydroxyethyl acrylate copolymer/acryloyldimethyltaurate acrylate copolymer (INCI name),
 with the mixture $M'_1$/mixture $M'_2$/copolymer mass ratio being 12/3/2.

It can indeed be noted that the hydroxyethyl acrylate copolymer/acryloyldimethyltaurate acrylate copolymer is not able to form a gel with an apolar oil. This type of polymer can possibly form a gel with an aqueous phase.

Preparation of the Gelled Composition:

The gelled composition can be prepared according to any method well known to those skilled in the art in order to formulate a gel. For example, the gelled composition according to the invention can be prepared by a method that comprises the following steps:
 Mixing the hydrocarbon oil and the gelling agent, in particular the gelling polymer;

Heating the mixture of hydrocarbon oil and gelling agent, in particular gelling polymer, more preferably to a temperature ranging from 40° C. to 180° C. or ranging from 60° C. to 150° C.;

Stirring the heated mixture until a homogeneous mixture is obtained;

Cooling the homogeneous mixture typically to ambient temperature (about 25° C.).

According to another embodiment, the hydrocarbon oil is heated beforehand before mixing with the gelling agent, in particular the gelling polymer.

Additives:

The gelled composition according to the invention can also be mixed with any adjuvant or additive normally used in the fields considered and in particular in the cosmetic, dermatological or pharmaceutical fields. Of course, those skilled in the art will make sure to choose any additive or additives of the composition according to the invention in such a way that the advantageous properties intrinsically attached to the gelled composition in accordance with the invention are not or are substantially not, altered by the addition under consideration. Among the conventional additives able to be contained (according to the water-soluble or liposoluble nature of these adjuvants), mention can be made in particular of anionic foaming surfactants (such as sodium lauryl ether sulphate, sodium alkyl phosphate, sodium trideceth sulphate), amphoteric surfactants (such as alkyl betaine, disodium cocoamphodiacetate) or non-ionic surfactants with an HLB greater than 10 (such as POE/PPG/POE, Alkylpolyglucoside, polyglyceryl-3hydroxylauryl ether); preservatives such as benzalkonium chloride; sequestering agents (EDTA); antioxidants; perfumes; dyestuffs such as soluble dyes, pigments and nacres; mattifying, tensor, whitening or exfoliating fillers; sunscreen filters; cosmetic or dermatological active ingredients and agents that have for effect to improve the cosmetic properties of the skin, hydrophilic or lipophilic; electrolytes. The quantities of these various adjuvants are those conventionally used in the field considered, and for example from 0.01 to 20% of the total weight of the composition. As active ingredients that can be used in the gelled composition of the invention, mention can be made for example of water-soluble or liposoluble vitamins such as vitamin A (retinol or beta-carotene), vitamin E (tocopherol), vitamin C (ascorbic acid), vitamin B5 (panthenol), vitamin B3 (niacinamide), the derivatives of these vitamins (in particular esters) and mixtures thereof; antiseptics; active antibacterial ingredients such as 2,4,4'-trichloro-2'-hydroxy diphenyl ether (or triclosan), 3,4,4'-trichlorocarbanilide (or triclocarban); anti-seborrheics; antimicrobials such as benzoyl peroxide, niacin (vit. PP); slimming agents such as caffeine; optical brighteners, and any active ingredient for the final purpose of the composition, and mixtures thereof.

Cosmetic, Dermatological or Pharmaceutical Composition:

The present invention also has for object a cosmetic, dermatological or pharmaceutical composition comprising the gelled composition according to the invention and:
- at least one fatty substance chosen from among: vegetable oils, vegetable butters, fatty alcohols and ethers, oily esters, alkanes and silicone oils, preferably from among oily esters, and/or
- at least one additive chosen from among the aforementioned additives, preferably from among anionic foaming surfactants (such as sodium lauryl ether sulphate, sodium alkyl phosphate, sodium trideceth sulphate), amphoteric surfactants (such as alkyl betaine, disodium cocoamphodiacetate) or non-ionic surfactants with an HLB greater than 10 (such as POE/PPG/POE, Alkylpolyglucoside, polyglyceryl-3hydroxylauryl ether).

The fatty substance is preferably chosen from among fatty substances that have a low polarity.

Examples of vegetable oils are in particular wheat germ, sunflower, grape seed, sesame, corn, apricot, castor, shea, avocado, olive, soybean oil, sweet almond, palm, rapeseed, cotton, hazelnut, macadamia, jojoba, alfalfa, poppy, squash, sesame, pumpkin, rapeseed, blackcurrant, evening primrose, millet, barley, quinoa, rye, safflower seed, candlenut, passion flower, rose hip or camellia oils.

Vegetable butters are fatty substances that have the same properties as vegetable oils. The difference between the two consists in the fact that butters are in solid form at ambient temperature. Also, contrary to vegetable oils, the raw material from which a butter is extracted (pulp, seeds or almonds) is heated after having been ground for the extraction of the fat. As vegetable oils, butters can be refined in order to provide better preservation, neutralise odours, improve the colour and the consistency. Rich in antioxidants and nourishing the cosmetic properties of vegetable butters improve the elasticity of the skin, protect from external aggressions by leaving a protective film on the epidermis and thus reducing dehydration, repair and soothe by regenerating the natural hydrolipidic film of the skin. Examples of vegetable butters are in particular shea butter, cocoa butter, mango butter, shorea butter or olive butter.

Fatty alcohols and ethers are fatty waxy long-chain substances with remarkable properties in particular film-forming, emollient, moisturising, softening and protective properties. They act as moisturising oils and as emulsifiers. Examples of fatty alcohols or ethers are: cetyl Alcohol, Stearyl Alcohol, myristyl alcohol, auryl alcohol, behenyl alcohol, cetearyl alcohol, dicaprylyl ethers, stearyl ethers or octyldodecanol (identified by their INCI name).

Oily esters or esterified oils are the product of a reaction between fatty acids (longer chain acids, such as for example stearic acid, oleic acid, palmitic acid) and alcohols (fatty alcohols or polyols such as glycerol). These oils can contain substances coming from petrochemicals, as is the case for Isopropyl Palmitate. Examples of oily esters are caprylic capric triglyceride, coco caprylate caprate, oleyl erucate, oleyl linoleate, decyl oleate or PPG-3 benzyl ether myristate (identified by their INCI name).

The term "silicone oils or polysiloxanes" means an oil comprising at least one silicon atom, and in particular at least one Si—O group. As silicone oil, mention can be made in particular of phenylpropyldimethylsiloxysilicate, dimethicones or cyclopentasiloxane (identified by their INCI name).

This cosmetic, dermatological or pharmaceutical composition comprises a physiologically acceptable medium, i.e. which does not have any deleterious secondary effects and in particular which does not produce any unacceptable redness, flare-ups, tightness or stinging for a user. This medium optionally comprises water and/or at least one oil as a fatty substance, in addition to the aforementioned gelled composition.

According to an embodiment the cosmetic, dermatological or pharmaceutical composition has a content of gelled composition as described hereinabove ranging from 0.5 to 80%, preferably from 1 to 50% and advantageously from 5 to 30% by weight relative to the total weight of the composition.

Preferably, when the fatty substance is chosen from among vegetable oils, the fatty substance will represent preferably less than 50% by weight, even more preferably less than 30% by weight, of the weight of the cosmetic, dermatological or pharmaceutical composition.

Preferably, when the fatty substance is chosen from among silicone oils or polysiloxanes, the fatty substance will represent preferably less than 40% by weight, even more preferably less than 30% by weight, of the weight of the cosmetic, dermatological or pharmaceutical composition.

The cosmetic, dermatological or pharmaceutical composition according to the invention can thus be an anhydrous composition, an emulsion such as a water-in-oil emulsion (W/O), an oil-in-water emulsion (O/W) or a multiple emulsion (in particular W/O/W or O/W/O), a nano-emulsion, or a dispersion, according to the additives optionally introduced and/or according to an aqueous phase optionally introduced.

When the composition is an emulsion of the oil-in-water type, preferably, the invention does not relate to an emulsion for topical use of the oil-in-water (E) type comprising for 100% of its mass:
From 50% to 90% by weight, of a cosmetically acceptable aqueous phase (A),
From 10% to 50% by weight, of a fatty phase (F) comprising for 100% of its mass:
From 10% to 50% by weight, more particularly from 15% to 40% by weight of a mixture (M1) of linear or branched, cyclic or acyclic saturated hydrocarbons among which at least 95% by weight comprises from fifteen to nineteen carbon atoms;
From 0.5% to 15% by weight, of at least one surfactant of the oil-in-water type,
From 5% to 30% by weight, of at least one protective agent against the ultraviolet radiation from the sun,
From 0% to 80% by weight, of at least one oil and/or one wax, with the understanding that such an oil and/or such a wax does not satisfy the definition of the mixture (M1);

When the composition is an emulsion of the oil-in-water type, preferably, the invention does not relate to an emulsion of the oil-in-water type (E) comprising for 100% of its mass:
from 40% to 90%, by weight of a cosmetically acceptable aqueous phase (A) that comprises for 100% of its mass from 1% by weight to 30% by weight of glycerol, and
from 10% to 60% by weight of a fatty phase (F) comprising for 100% of its mass from 1% to 25% by weight of a mixture (M1) of linear or branches, cyclic or acyclic saturated hydrocarbons among which at least 95% by weight comprises from fifteen to nineteen carbon atoms and from 0.5% to 15% of at least one surfactant of the oil-in-water type.

The cosmetic, dermatological or pharmaceutical composition according to the invention can constitute for example a composition for make-up removal or for cleaning the skin, lips, a sunscreen composition (U.V. protection), or after-sun, a composition for the massaging of the skin, a shower care balm composition, an antiperspirant composition, a mask composition, a repair balm composition, a scrubbing and/or exfoliating composition for the face as well as for the hands (when it contains exfoliating particles), a make-up composition, a shaving composition, and after-shave balm composition, a perfumed composition, a composition for wipes.

The composition of the invention is advantageously characterised by the fact that it has a stability of a duration greater than or equal to 4 weeks, advantageously greater than or equal to 6 weeks, with the stability being evaluated after storage without stirring at ambient temperature, at 40° C. and at 50° C. and corresponding to a visual evaluation of the coloration and of the aspect as well as an olfactory evaluation and/or a measurement of the viscosity.

Use of the Gelled Composition:

The invention further has for object the cosmetic, dermatological or pharmaceutical use of the composition as defined hereinabove for a topical application, on the skin, the lips or the appendages (including the nails, the scalp and the hair).

The invention further has for object the cosmetic, dermatological or pharmaceutical use of the cosmetic, dermatological or pharmaceutical composition as defined hereinabove as a skin care product (serums, cremes, balms, etc.), as a hygiene product, as a sunscreen/after-sun product, as a make-up product, as a makeup remover, as a perfumed product, as an antiperspirant product, as a lip care product, such as a gloss or moisturising sticks for lips.

The gelled composition according to the invention can be used, preferably as an active ingredient, for improving the appearance of the skin and/or for strengthening hair and/or for slowing down ageing and/or for delaying the appearance of wrinkles and/or for reducing wrinkles and/or for tightening the skin. In particular, the inventors have discovered that the gelled composition had an antioxidant effect as well as an anti-radical effect.

The gelled composition according to the invention can be used, preferably as an active ingredient, as a drug.

According to an aspect of the invention, the gelled composition can be used as an antioxidant agent and/or anti-radical agent and/or anti-inflammatory agent and/or anti-apoptotic and/or antibacterial and/or antifungal agent.

The invention further has for object a cosmetic, dermatological or pharmaceutical method for treating the skin, comprising at least one step of applying on the skin, the lips and/or the appendages a composition as defined hereinabove.

The composition of the invention can also be used for the formulation of cosmetic compositions, dermatological compositions or pharmaceutical compositions that comprise other components or other phases than those described hereinabove. This can in particular be the formulation of care, hygiene, make-up compositions.

Method of Cosmetic Treatment:

Finally, the invention also relates to a method of cosmetic treatment comprising at least one step of applying, preferably by spreading, on the skin, the lips or the appendages, compositions according to the invention.

Examples

In the rest of the present description, examples are given for the purposes of information of the present invention and do not aim in any case to limit the scope thereof.

Gelled Composition:

A gelled composition comprising 90% by weight of a hydrocarbon oil and 10% by weight of a linear diblock copolymer based on styrene and ethylene/propylene with a content of polystyrene of 28% by weight/weight of the polymer. The gelled composition was prepared according to a method as described in the present invention.

Table 1 groups together the physical-chemical properties of the hydrocarbon oil.

TABLE 1

| physical-chemical properties of the hydrocarbon oil | |
| --- | --- |
| Characteristics | Hydrocarbon oil |
| Aromatics (ppm) | <20 |
| Sulphur (ppm) | 0.11 |
| % iso paraffins (w/w) | 96.2 |
| % n-paraffins (w/w) | 3.8 |
| % naphthenics (w/w) | 0 |
| C13 (iso) | 0 |
| C14 (iso) | 0 |
| C15 (iso) | 0 |
| C16 (iso) | 1.58 |
| C17 (iso) | 14.17 |
| C18 (iso) | 79.69 |
| C19 (iso) | 0.12 |
| C20 (iso) | 0.38 |
| C27 (iso) | 0.29 |
| Quantity of carbons of biological origin (%) | >98 |

TABLE 1-continued physical-chemical properties of the hydrocarbon oil

| Characteristics | Hydrocarbon oil |
|---|---|
| Initial boiling point (° C.) | 293.6 |
| Boiling point 5% (° C.) | 296.7 |
| Boiling point 50% (° C.) | 298.5 |
| Boiling point 95% (° C.) | 305.3 |
| Final boiling point (° C.) | 324.1 |
| OECD biodegradability (28 days) (%) | 83 |
| Refractive index at 20° C. | 1.4394 |
| Density at 15° C. (kg/m3) | 787.2 |
| Flash point (° C.) | 149 |
| Kinematic Viscosity at 40° C. (cSt) | 3.87 |
| Vapour pressure at 20° C. (kPa) | <0.01 |
| Aniline point (° C.) | 93.2 |

The following standards and methods were used to measure the properties hereinabove:
flash point: EN ISO 2719
density at 15° C.: EN ISO 1185
viscosity at 40° C.: EN ISO 3104
aniline point: EN ISO 2977
boiling point: ASTM D86
biodegradability: OECD method 306
refractive index at 20° C.: ASTM D 1218
vapour pressure: calculated according to methods well known to those skilled in the art Evaluation of the Miscibility of the Gelled Composition with Fatty Substances The fatty substances tested are:
a vegetable oil: meadowfoam seed oil (according to the INCI name) that has a density at 20° C. of 0.91 and which comprises:
58.0-64.0% by weight of gadoleic acid (C20:1)
10.0-14.0% by weight of erucic acid (C22:1 d13)
3.0-6.0% by weight of docosenoic acid (C22:1 d5)
15.0-21.0% by weight of docosadienoic acid (C22:2)
In relation to the total weight of the vegetable oil.
An oily ester: isononyl isononanoate (according to the INCI name), commercially available.
A silicone oil: cyclopentasiloxane (according to the INCI name), commercially available.

The manipulation consists in observing the miscibility of the gelled composition with the fatty substances, by proceeding with the adding of the fatty substance to be tested into the gelled composition by increasing percentages by weight: 10%, 25%, 50%, 75% and 90%. These manipulations are carried out continuously. The mixture is observed between each addition. The adding is carried out in the same recipient.

The experiments are carried out based on starting with 45 g of gelled composition and ending with 450 g. Indeed, the additions are carried out as such based on 45 g, present in the beaker:
10%: adding 5 g of fatty substances to be tested.
25%: adding 10 g of fatty substances to be tested in the previously-obtained mixture (15*100/60=25).
50%: adding 30 g of fatty substances to be tested in the previously-obtained mixture.
75%: adding 90 g of fatty substances to be tested in the previously-obtained mixture.
90%: adding 270 g of fatty substances to be tested in the previously-obtained mixture.

The final mixtures are stored in glass jars and are observed at D+1. A mixture is said to be non-miscible when sediments are observed visually.

It was thus observed that:
The gelled composition according to the invention is miscible with the vegetable oil, when the vegetable oil is present in a quantity ranging up to 50% by weight.
The gelled composition according to the invention is miscible with the oily ester, when the oily ester is present in a quantity ranging up to 90% by weight.
The gelled composition according to the invention is miscible with the silicone oil, when the silicone oil is present in a quantity ranging up to 25% by weight.

Evaluation of the Compatibility of the Gelled Composition with Emulsifiers

Preparation of the Emulsions:
The following oil-in-water (O/W) emulsifiers were tested:
An anionic emulsifier: Sensanov WR® (available from Seppic), corresponding to the product C20-22 Alkyl Phosphate & C20-22 Alcohols (according to the INCI name).
Two non-ionic emulsifiers:
Montanov® 68 (available from Seppic), which corresponds to Cetearyl Alcohol (and) Cetearyl Glucoside (according to the INCI name).
Simulsol® 165 (available from Seppic), corresponding to the product PEG-100 Stearate (and) Glyceryl Stearate (according to the INCI name).
A cationic emulsifier: Incronat® Behenyl TMS (available from Croda), corresponding to the product Cetearyl Alcohol, Behentrimonium Methosulphate (according to the INCI name).
A water-in-oil (W/O) emulsifier was also tested:
Non-ionic emulsifier: Abil® EM180 (available from Evonik), corresponding to the product Cetyl PEG/PPG-10/1 Dimethicone (according to the INCI name).

Emulsions 1 to 5 were prepared using 5 emulsifiers described hereinabove. Table 2 hereinbelow indicates the composition of the emulsions 1 to 5 tested.

Emulsions (H/E) 1 to 4 were prepared according to the following operating procedure:
The water is weighed, stirred and heated to 50° C. At 50° C., the Glycerine and Xanthan Gum premix is poured in with rapid stirring. The stirring is maintained until a homogeneous phase is obtained. Finally the heating is continued to 75-80° C. (according to the emulsifier).
The fatty phase is weighed, stirred and heated to 75-80° C.
At 75-80° C., the fatty phase is progressively poured into the aqueous phase under rapid stirring. The cooling is then initiated.
At 72-75° C. the emulsion is stirred using a device of the Turrax® type 30 seconds at 9,500 rpm.
The cooling is then continued.
At 50° C., the preservative is poured into the emulsion under stirring.
At 25° C., the pH is measured and adjusted if necessary (either with a solution of soda at 10%, or with a solution of citric acid at 50%): with the desired range between 5.00 and 7.00.

The emulsion (E/H) 5 was prepared according to the following operating procedure:
The water and the glycerine are weighed, placed under stirring. The salt, then the preservative are added thereto.
The emulsifier is weighed, placed under stirring. The ester is added thereto under stirring, then the gelled composition
When the two phases are homogeneous: the aqueous phase is added slowly into the fatty phase, drop by drop.
The adding can be accelerated when more than one-third of the aqueous phase has been added.

TABLE 2

Description of the emulsions tested 1 to 5 (percentages expressed by weight relative to the total weight of the emulsion)

| | | Emulsion 1 | Emulsion 2 | Emulsion 3 | Emulsion 4 | Emulsion 5 |
|---|---|---|---|---|---|---|
| Fatty phase | Sensanov WR® | 3.00% | | | | |
| | Montanov® 68 | | 5.00% | | | |
| | Simulsol® 165 | | | 5.00% | | |
| | Incronat® Behenyl TMS | | | | 5.00% | |
| | Abil® EM180 | | | | | 2.00% |
| | Cetearyl Alcohol | 2.00% | 2.00% | 2.00% | 2.00% | |
| | Gelled composition | 5.00% | 5.00% | 5.00% | 5.00% | 5.00% |
| | Ester (isononyl Isononanoate) | 10.00% | 10.00% | 10.00% | 10.00% | 10.00% |
| Aqueous phase | Demineralised water | Qsp 100% | Qsp 100% | Qsp 100% | Qsp 100% | Qsp 100% |
| | Glycerine | 1.00% | 1.00% | 1.00% | 1.00% | 1.00% |
| | Xanthan gum | 0.25% | 0.25% | 0.25% | | |
| | preservative (methylisothiazolinone) | 0.10% | 0.10% | 0.10% | 0.10% | 0.10% |
| | NaCl (salt) | | | | | 0.50% |
| | Temperature for the preparation of the emulsion | 80° C.[1] | 75° C. | 75° C. | 80° C.[1] | 23° C. |
| | Viscosity at 25° C. at D + 1 (mPa · s) | 16,500 | 5,500 | 9,000 | 9,000 | 120,000 |

[1]The pH was adjusted using a solution of soda at 10%

Observation Under the Microscope of Each Emulsion:

The compatibility of the gelled composition according to the invention with the emulsifiers was evaluated visually via an observation under the microscope of each emulsion.

Stability of the Viscosity Over Time:

The viscosity of the emulsions was also measured using the Brookfield RV DVII+PRO for 1 minute in 200 g jars having been thermostated beforehand between 24.5 and 25.5° C. In particular, the change in the viscosity over time was evaluated: at D0, D+1 (24 hours), 2 weeks, 4 weeks and 8 weeks. A score "+" means satisfactory stability and a score "++" means very good stability.

Stability of the pH Over Time:

The pH is also measured over time from D0 (initially) to 8 weeks. A score "+" means satisfactory stability with a downward trend over time and in temperature, a score "++" means good stability with a slight downward trend in temperature and a score "+++" means very good stability.

Stability at Centrifugation:

A centrifugation is implemented on the emulsions at D+1 (24 hours), for 1 h30 at 4,000 rpm. A score "+" means satisfactory stability with formation of a small base of water and a score "++" means very good stability without any instability.

The results of these tests are gathered together in table 3 hereinbelow.

TABLE 3 evaluation of the properties of emulsions 1 to 5

| | Emulsion 1 | Emulsion 2 | Emulsion 3 | Emulsion 4 | Emulsion 5 |
|---|---|---|---|---|---|
| Observation under the microscope | Homogeneous, sparse, coarse droplets | Homogeneous, very dense, moderately thin droplets | Homogeneous, dense, relatively thin droplets | Homogeneous, moderately dense, moderately thin droplets | Homogeneous, very dense, very thin droplets |
| Stability of the viscosity | ++ | + | ++[1] | ++[1] | ++ |
| Stability of the pH | + | +++ | + | ++ | (2) |
| Stability (centrifugation) | ++ | ++ | ++ | + | ++ |

[1]starting from D + 1
(2) Not applicable to this type of emulsion (E/H)

In conclusion, it can be noted that the gelled composition according to the invention is compatible with different types of emulsifiers.

Preparation of Cosmetic Formulations Comprising the Gelled Composition

Creme for the Face

A creme for the face having the composition indicated in the table 4 hereinbelow was prepared. The content of each ingredient is indicated as a percentage by weight relative to the total weight of the composition of creme. For the various ingredients of the gelled composition prepared beforehand, the INCI name (EU) is given.

TABLE 4 composition of the creme for the face

| Preparation phase | Commercial name | ingredients | Content in % by weight |
|---|---|---|---|
| A | MONTANOV ® 68 | CETEARYL ALCOHOL CETEARYL GLUCOSIDE GLUCOSE AQUA | 5.00 |
| | CUTINA ® PES | PENTAERYTHRITYL DISTEARATE | 3.00 |
| | JEENATE ® 2H | POLYETHYLENE | 2.00 |
| | KARITE ® CP | *BUTYROSPERMUM PARKII* BUTTER | 2.00 |
| | MASSOCARE ® TH | TRIETHYLHEXANOIN | 5.00 |
| | LANOL ® 99 | ISONONYL ISONONANOATE | 4.00 |
| | | Gelled composition | 5.00 |
| B | DEMINERALISED WATER | AQUA | 68.12 |
| | EDETA ® BD | DISODIUM EDTA AQUA | 0.10 |
| | GLYCERINE CODEX ® | GLYCERIN | 2.50 |
| | RHODICARE ® T | XANTHAN GUM AQUA | 0.30 |
| | CHLORPHENESIN ® BP 73 | CHLORPHENESIN AQUA | 0.25 |
| C | PHENOXETOL ® | PHENOXYETHANOL | 0.80 |
| | SEPINOV ® EMT10 | HYDROXYETHYL ACRYLATE/SODIUM ACRYLOYLDIMETHYL TAURATE COPOLYMER SORBITAN ISOSTEARATE POLYSORBATE 60 AQUA | 0.80 |
| D | JUVENESSENCE ® | CAPRYLIC/CAPRIC TRIGLYCERIDE ALGAE EXTRACT | 1.00 |
| | NORA ® SA FML00190 | PERFUME | 0.13 |

Method of Preparing the Creme for the Face:

a) Place the ingredients of the phase A under stirring and heat to 75° C. until a homogeneous phase is obtained.

b) Weigh the water and the edeta BD. Place under stirring and begin to heat. At 50° C. introduce the glycerine+rhodicare T premix. Continue stirring until a homogenous phase is obtained, while still continuing to heat to 75° C. At 75° C. introduce the chlorphenesine. Then at 75° C., under 1,200 rpm, produce the emulsion by pouring the phase A (obtained in the step a) into the phase B (obtained in the step b)). Begin to cool by maintaining the stirring speed. At 72° C. turrax 30 s at 9,500 rpm then continue the cooling under moderate stirring.

c) At 50° C. introduce the phenoxetol, then sprinkle the sepinov EMT10. Maintain under rapid stirring until a homogeneous product is obtained. Then continue the cooling under moderate stirring.

d) At ambient temperature (23° C.) successively add the components of the phase D. Measure the pH and adjust it if necessary with a solution of soda at 10% in order to obtain a pH between 5.50 and 6.00.

Moisturising Body Milk

A moisturising body lotion that has the composition indicated in the table 5 hereinbelow was prepared. The content of each ingredient is indicated as a percentage by weight relative to the total weight of the composition of creme. For the various ingredients of the gelled composition prepared beforehand, the INCI name (EU) is given.

TABLE 5 composition of the body milk

| Preparation phase | Commercial name | ingredients | Content in % by weight |
|---|---|---|---|
| A | MONTANOV ® L | C14-22 ALCOHOLS C12-20 ALKYL GLUCOSIDE | 3.00 |
| | TEGO ALKANOL ® 1618 | CETEARYL ALCOHOL | 1.00 |
| | TEGO ALKANOL ® 16 | CETYL ALCOHOL | 1.00 |
| | LANOL ® 99 | ISONONYL ISONONANOATE | 5.00 |
| | DUB ® IPP | ISOPROPYL PALMITATE | 4.00 |
| | | Gelled composition | 2.00 |
| B | DEMINERALISED WATER | AQUA | 74.25 |

TABLE 5-continued composition of the body milk

| Preparation phase | Commercial name | ingredients | Content in % by weight |
|---|---|---|---|
| | EDETA ® BD | DISODIUM EDTA AQUA | 0.10 |
| | ZEMEA ® PROPANEDIOL | PROPANEDIOL AQUA | 3.00 |
| | RHODICARE ® T | XANTHAN GUM AQUA | 0.30 |
| | SEPIPLUS ® S | HYDROXYETHYL ACRYLATE/SODIUM ACRYLOYLDIMETHYL TAURATE COPOLYMER POLYISOBUTENE PEG-7 TRIMETHYLOLPROPANE COCONUT ETHER AQUA SORBITAN ISOSTEARATE | 0.50 |
| | CHLORPHENESIN ® BP 73 | CHLORPHENESIN AQUA | 0.25 |
| C | PENOXETOL ® | PHENOXYETHANOL | 0.80 |
| | MIRASIL ® CM5 | CYCLOPENTASILOXANE | 1.00 |
| D | AQUAXYL ® | XYLITYLGLUCOSIDE ANHYDROXYLITOL AQUA XYLITOL GLUCOSE | 3.00 |
| | BERYL ® SA FML00314 | PERFUME MENTHOL GERANIOL BHT TOCOPHEROL | 0.80 |

Method for Preparing the Body Milk:
a) Place the compounds of the phase A under stirring and heat to 80° C. until a homogeneous phase is obtained.
b) Place the EDTA and the water of the phase B under stirring until a homogeneous phase is obtained, while heating to 50° C. At 50° C., introduce a zemea and rhodicare T premix and continue heating and stirring until 80° C. while verifying the obtaining of a homogeneous phase. At 80° C., under rapid stirring, introduce the sepiplus S and maintain under stirring until a homogeneous phase is obtained. At 80° C., under 1,200 rpm, introduce the phase A (obtained in the step a) into the phase B (obtained in the step b)) the begin cooling by maintaining the stirring speed. At 72° C. sprinkle the chlorphenesine then turrax 30 s at 9,500 rpm. Continue the cooling under moderate stirring.
c) At 50° C. successively introduce the components of the phase C then continue the cooling under moderate stirring.
e) At 35° C., successively introduce the components of the phase D, verifying the correct homogeneity between each addition. Measure the pH and adjust it if necessary in order to obtain a pH between 5.50 and 6.00.

The invention claimed is:

1. A gelled composition consisting of:
from 70 to 90% by weight of at least one hydrocarbon oil that has a content by weight of isoparaffins ranging from 95 to 100%, a content by weight of normal paraffins ranging from 0 to 5%, a content by weight of naphthenic compounds less than or equal to 1%, a content by weight of aromatic compounds less than or equal to 300 ppm, and a content of carbon of biological origin greater than or equal to 90% relative to the total weight of the hydrocarbon oil, wherein the hydrocarbon oil has a boiling temperature ranging from 230 to 340° ° C., according to the standard ASTM D86, wherein the hydrocarbon oil has a flash point greater than or equal to 110° C. according to the standard EN ISO 2719 and a vapor pressure at 20° C. less than or equal to 0.01 kPa, and
from 10 to 30% by weight of at least one gelling polymer chosen from among diblock copolymers comprising at least one styrene monomer and at least one monomer chosen from among ethylene, propylene, butadiene, and isoprene,
relative to the total weight of the gelled composition,
wherein the hydrocarbon oil comprises:
isoparaffins having 16 carbon atoms, isoparaffins having 17 carbon atoms and isoparaffins having 18 carbon atoms in a combined quantity ranging from 80 to 98% by weight, relative to the total weight of the hydrocarbon oil, or
isoparaffins having 17 carbon atoms and isoparaffins having 18 carbon atoms in a combined quantity ranging from 80 to 98% by weight, relative to the total weight of the hydrocarbon oil.

2. The gelled composition according to claim 1, wherein the gelling polymer is chosen from among styrene/butadiene copolymers, styrene/isoprene copolymers, hydrogenated styrene/butadiene copolymers, hydrogenated styrene/isoprene copolymers, hydrogenated polyisoprene crosspolymers, polyisoprene homopolymers, hydrogenated styrene thermoplastic homopolymers, liquid rubbers, and mixtures thereof.

3. The gelled composition according to claim 1, wherein the hydrocarbon oil is chosen from among non-cyclic isoparaffins comprising from 14 to 18 carbon atoms.

4. The gelled composition according to claim 1, wherein the hydrocarbon oil comprises:

a content by weight of isoparaffins ranging from 98 to 100% relative to the total weight of the hydrocarbon oil;

a content of carbon of biological origin greater than or equal to 95%;

a content by weight of normal paraffins less than or equal to 2% relative to the total weight of the hydrocarbon oil; and/or a content by weight of naphthenic compounds less than or equal to 0.5%, relative to the total weight of the hydrocarbon oil; and/or a content by weight of aromatic compounds less than or equal to 100 ppm relative to the total weight of the hydrocarbon oil; and/or a biodegradability at 28 days of at least 60%, measured according to the standard OECD 306.

5. The gelled composition according to claim 1, wherein the hydrocarbon oil is obtained by a method of catalytic hydrogenation at a temperature from 80 to 180° C. and at a pressure from 50 to 160 bars of a deoxygenated and/or isomerised feedstock of biological origin.

6. A cosmetic, dermatological or pharmaceutical composition comprising at least one gelled composition according to claim 1.

7. The cosmetic, dermatological or pharmaceutical composition according to claim 6, comprising at least one fatty substance chosen from among: vegetable oils, hydrocarbon oils other than the hydrocarbon oil of the gelled composition, vegetable butters, fatty alcohols and ethers, oily esters, alkanes and silicone oils and/or at least one additive.

8. A method for the treatment of the skin or hair or lips, comprising a step of topically applying the gelled composition according to claim 1, or a cosmetic, dermatological or pharmaceutical composition including said gelled composition according to claim 1.

9. The method according to claim 8, comprising a step of anti-ageing treatment.

10. A method of therapeutic treatment comprising administering the gelled composition according to claim 1 or a cosmetic, dermatological or pharmaceutical composition including said gelled composition according to claim 1 as a drug.

11. The method according to claim 10, comprising administering the gelled composition or the cosmetic, dermatological or pharmaceutical composition as an antioxidant and/or anti-radical agent and/or anti-inflammatory agent and/or anti-apoptotic and/or antibacterial and/or antifungal agent.

12. The cosmetic, dermatological or pharmaceutical composition according to claim 6, comprising the gelled composition in a quantity ranging from 0.5 to 80% by weight relative to the total weight of the composition.

13. The method according to claim 8, wherein the gelled composition or the cosmetic, dermatological or pharmaceutical composition is applied as a care product for the skin or hair, as a make-up product, as a hair care product, as a makeup remover, as a perfumed product, as a sunscreen product, as a lip care product.

14. The gelled composition according to claim 1, having a viscosity measured at 23° C. ranging from 3 to 750,000 mPa·s.

* * * * *